US010381106B2

(12) United States Patent
Plattner et al.

(10) Patent No.: US 10,381,106 B2
(45) Date of Patent: *Aug. 13, 2019

(54) EFFICIENT GENOMIC READ ALIGNMENT IN AN IN-MEMORY DATABASE

(71) Applicant: Hasso-Plattner-Institut fuer Softwaresystemtechnik GmbH, Potsdam (DE)

(72) Inventors: Hasso Plattner, Schriesheim (DE); Matthieu-Patrick Schapranow, Berlin (DE); Emanuel Ziegler, Heidelberg (DE)

(73) Assignee: Hasso-Plattner-Institut Fuer Softwaresystemtechnik GmbH, Potsdam (DE)

( * ) Notice: Subject to any disclaimer, the term of this patent is extended or adjusted under 35 U.S.C. 154(b) by 784 days.

This patent is subject to a terminal disclaimer.

(21) Appl. No.: 14/165,123

(22) Filed: Jan. 27, 2014

(65) Prior Publication Data

US 2014/0214334 A1 Jul. 31, 2014

Related U.S. Application Data

(60) Provisional application No. 61/757,506, filed on Jan. 28, 2013.

(51) Int. Cl.
*G01N 33/48* (2006.01)
*G16B 30/00* (2019.01)
(Continued)

(52) U.S. Cl.
CPC ............. *G16B 30/00* (2019.02); *G16B 50/00* (2019.02); *G16B 45/00* (2019.02)

(58) Field of Classification Search
None
See application file for complete search history.

(56) References Cited

U.S. PATENT DOCUMENTS

2013/0073214 A1* 3/2013 Hyland .................. G06F 19/22
702/19

FOREIGN PATENT DOCUMENTS

EP 2 040 180 A1 3/2009

OTHER PUBLICATIONS

Hoffmann, S. et al, "Fast Mapping of Short Sequences with Mismatches, Insertions and Deletions Using Index Structures", PLoS Computational Biology, Sep. 2009, vol. 5, Issue 9, pp. 1 to 10.
(Continued)

*Primary Examiner* — Larry D Riggs, II
(74) *Attorney, Agent, or Firm* — Ewers & Hasselmann PLLC

(57) ABSTRACT

A high performance, low-cost, gapped read alignment algorithm is disclosed that produces high quality alignments of a complete human genome in a few minutes. Additionally, the algorithm is more than an order of magnitude faster than previous approaches using a low-cost workstation. The results are obtained via careful algorithm engineering of the seeding based approach. The use of non-hashed seeds in combination with techniques from search engine ranking achieves fast cache-efficient processing. The algorithm can also be efficiently parallelized. Integration into an in-memory database infrastructure (IMDB) leads to low overhead for data management and further analysis.

20 Claims, 7 Drawing Sheets

Specification includes a Sequence Listing.

(51) Int. Cl.
G16B 50/00 (2019.01)
G16B 45/00 (2019.01)

(56) References Cited

OTHER PUBLICATIONS

Malhis, N. et al, "High quality SNP calling using Illumina data at shallow coverage", Bioinformatics Original Paper, vol. 26, No. 8, 2010, pp. 1029 to 1035, Oxford University Press.

Sivam, D. et al, "The C.A.Ve. Software Tool for Genome Assembly.", AMIA 2003 Symposium Proceedings, p. 1009, XP001206536.

Lam, H. et al, "Detecting and annotating genetic variations using the HugeSeq pipeline", Correspondence, Nature Biotechnology, vol. 30, No. 3, Mar. 2012, pp. 226 to 229.

Langmead, B. et al, "Fast gapped-read alignment with Bowtie 2", Brief Communications, Nature Methods, vol. 9, No. 4, Apr. 2012, pp. 357 to 360.

Search Report of the European Patent Office dated Jul. 18, 2013 in the corresponding European patent application 13152885.3-1952.

Wassenberg, J. et al, "Engineering a Multi-Core Radix Sort", Euro-Par 2011, LNCS 6853, Part II, pp. 160 to 169, 2011, Springer-Verlag Berlin Heidelberg.

Schatz, M. et al, "CloudBurst: highly sensitive read mapping with MapReduce", Bioinformatics Original Paper, vol. 25, No. 11, 2009, pp. 1363 to 1369.

Li, H. et al: "Fast and accurate long-read alignment with Burrows-Wheeler transform", Bioinformatics (Oxford, England) 26(5), pp. 589 to 595 advance access publication Jan. 15, 2010.

Li, R. et al, "SOAP2: an improved ultrafast tool for short read alignment", Bioinformatics (Oxford, England) 25(15), pp. 1966 to 1967 (Aug 2009).

Zaharia, M., "Faster and More Accurate Sequence Alignment with SNAP" pp. 1 to 10, arXiv:1111.5572v1 [cs.DS] Nov. 23, 2011.

Siragusa, E. et al, "Fast and accurate read mapping with approximate seeds and multiple backtracking", Nucleic Acids Research, pp. 1 to 8 (2013), Oxford University Press.

Li, H. et al, "A survey of sequence alignment algorithms for next-generation sequencing", Briefings in Bioinformatics vol. II (5), pp. 473 to 483 (2010).

Ferragina, P. et al, "Opportunistic Data Structures with Applications", In: Proceedings 41st Annual Symposium on Foundations of Computer Science, pp. 390 to 398, IEEE Comput. Soc (2000).

Needleman, S. et al, "A General Method Applicable to the Search for Similarities in the Amino Acid Sequence of Two Proteins", Journal of Molecular Biology 48(3), pp. 443 to 453 (Mar. 1970).

Smith, T. et al, "Identification of Common Molecular Subsequences", Journal of Molecular Biology, 147, (1981), pp. 195 to 197, Academic Press Inc. (London) Ltd.

U.S. Appl. No. 14/165,089, filed Jan. 27, 2014.

* cited by examiner

| Modification | Open left | Open right |
|---|---|---|
| First row initialised with 0 | w/o clipping | |
| First row and column initialised with 0 | w/ clipping | |
| Negative scores are set to 0 | w/ clipping | |
| Alignment ends w/ max score in last row | | w/o clipping |
| Alignment ends w/ max score in matrix | | w/ clipping |
| Backtracking stops at first row | w/o clipping | |
| Backtracking stops at zero score | w/ clipping | |

FIG. 4

EFFICIENT GENOMIC READ ALIGNMENT IN AN IN-MEMORY DATABASE

CROSS REFERENCE TO RELATED APPLICATION

This application claims benefit to U.S. provisional patent application Ser. No. 61/757,506, filed Jan. 28, 2013, the entire content of which is incorporated herein by reference.

FIELD OF THE INVENTION

The present application relates to a computer-based system for alignment of genomic sequence data by applying in-memory technology.

The material in the electronic sequence listing submitted as the text (.txt) file entitled "sequence_listing_14165123_ST25.txt" on Jan. 5, 2017, which was created on Jan. 4, 2016, and which has a file size of 1 KB, is herein incorporated by reference in its entirety.

BACKGROUND OF THE INVENTION

Next generation sequencing is maturing into a reliable diagnostics tool for widespread use. Sequencing technologies are leading to faster and cheaper sequencing and the work-flows have become more well defined. Within the next years, thousands to millions of human genomes will be completely sequenced and there will be an urgent need for analysis.

On the laboratory side, this development is made possible by dramatically improving throughput of sequencing machines that spit out sequencing data at ever higher rates and ever lower cost—in the last years the costs per sequenced base pair kept halving in periods of less than 6 month.

This progress is much faster than Moore's law for the cost of computing power which states halving intervals around 18 months. This moved into the focus that computation could become a severe bottleneck. The computationally most expensive and data intensive part of sequencing is aligning short imperfect reads (pieces of the genome of length≈100 base pairs) to a reference genome ($\approx 3 \times 10^9$ base pairs), i.e., given a read, to have to find where it best fits the reference genome and how it can be aligned by performing a small number of edits to account for reading errors and mutations (finding and scoring gaps in the alignment). This is a challenge, because it is not possible to have a priori information about the correct position. One also has to be aware that the computations cannot fully profit from Moore's law if they cannot exploit parallel processing and the memory hierarchy. In particular, sophisticated index data structures such as suffix arrays and suffix trees are difficult to construct in parallel and querying them imposes many cache faults. Originally, it has been suggested to use experience on parallel and memory hierarchy aware implementation of such data structures to attack this particular problem. But a closer analysis of the problem showed that with much simpler techniques it can get also much faster.

SUMMARY OF THE INVENTION

An object of the present invention therefore is to provide alignment tools which have a significantly better processing time.

Therefore, it is an object of the present invention to provide a high quality result as fast as possible, and, further, to automatically consolidate the query results of different database transactions.

This object is solved by the computer-based system and the method for processing (aligning) genomic sequence data by means of an in-memory database system disclosed herein.

A computer-based system according to the present invention is adapted for processing human or non-human nucleotide sequence data, which are provided as reads, comprising:
 a platform layer for holding process logic and an in-memory database system for processing nucleotide sequence data, wherein the platform layer comprises:
  a worker framework with a plurality of workers implemented as processes, wherein each worker is running on a computing node of a cluster consisting of multiple cores and wherein the workers are processing in parallel, wherein all results and intermediate results are stored in the in-memory database,
  an alignment coordinator, which is adapted to provide the in-memory database system with a modified alignment functionality.

According to a preferred embodiment of the present invention the alignment coordinator may be integrated in the worker framework.

According to a preferred embodiment the system further comprises:
 a user interface with at least a genome browser, which comprises
  a section for displaying a comparison of the nucleotide sequence and multiple referenced cell lines/genomes and/or a reference sequence and
  a section for displaying combined analysis information from multiple external databases and
  a section for selecting instructions for data processing, for particular pipeline configurations particularly for alignment of the genomic sequence data.

According to a further preferred embodiment the system further comprises an updater framework for automatically downloading and importing annotation updates (possibly comprising relevant research literature) from external sources into the in-memory database.

According to another aspect of the present invention a computer-implemented method is provided for processing human or non-human nucleotide sequence data with an in-memory database, comprising the method steps of:
 providing a cluster with a set of computing nodes with multiple cores, each implementing a worker for parallel data processing, and
 providing nucleotide sequence data as reads in the in-memory database and concurrently to sequencing processing data,
 wherein data processing comprises:
  aligning chunks of the read in parallel on the set of computing nodes and aggregating partial aligning results to an alignment result to be stored in the in-memory database system.

In a preferred embodiment the method further comprises one of the following method steps:
 Executing variant calling in parallel on the set of computing nodes and aggregating partial variant calling results to an variant calling result and/or
 Automatically analyzing the variant calling result by accessing an updater framework in the in-memory database, wherein the updater framework regularly and automatically checks a plurality of different external annotation sources for updates and which automatically downloads and imports said updates in the in-memory database.

In the following there is given a short definition of terms used within this application.

A chunk is to be construed as a part of the read. The amount of computing nodes and the size of the chunks is configurable.

The nucleotide sequence data may be human or non-human and may be DNA sequence data or RNA sequence data. In another embodiment of present invention the system may also be configured to process other genomic sequence data, like for example sequences of amino acids. The genomic sequence, however, mainly refers to a sequence which may be mapped to the alphabet comprising the letters C, G, A, T, and U, respectively, because the primary nucleobases are cytosine, guanine, adenine (DNA and RNA), thymine (DNA) and uracil (RNA), abbreviated as C, G, A, T, and U, respectively. In the following they are usually simply called bases (according to usual use in genetics).

The sequencer machine is a laboratory device which is adapted to automatically determine the precise order of nucleotides within a DNA molecule. Preferably it is a next-generation sequencing (NGS) device. The sequencing machine provides reads which are imported into the system. The NGS machine typically is not part of the system. It includes any method or technology that is used to determine the order of the four bases—adenine, guanine, cytosine, and thymine—in a strand of DNA. Generally, DNA sequencing may be used to determine the sequence of individual genes, larger genetic regions (i.e. clusters of genes or so called operons, as a functioning unit of genomic DNA containing a cluster of genes under the control of a single regulatory signal or promoter), full chromosomes or entire genomes. The resulting sequences may be used by researchers in molecular biology or genetics to further scientific progress or may be used for personalized medicine. For example cancer genome sequencing is the whole genome sequencing of a single, homogeneous or heterogeneous group of cancer cells. It is a biochemical laboratory method for the characterization and identification of the DNA or RNA sequences of cancer cell(s). Unlike whole genome (WG) sequencing which is typically performed on blood cells, saliva, epithelial cells or bone, cancer genome sequencing involves direct sequencing of primary tumor tissue, adjacent or distal normal tissue, the tumor micro environment such as fibroblast/stromal cells, or metastatic tumor sites. Similar to whole genome sequencing, the information generated from this technique include: identification of nucleotide bases (DNA or RNA), copy number and sequence variants, mutation status, and structural changes such as chromosomal translocations and fusion genes. Cancer genome sequencing is not limited to WG sequencing and can also include exome, transcriptome, and micronome sequencing. These methods can be used to quantify gene expression, miRNA expression, and identify alternative splicing events in addition to sequence data. The input data to be processed according to the invention may be provided as a FASTQ formatted file.

The term "modified alignment functionality" is to be construed as at least one of a plurality of different alignment algorithms being integrated into the in-memory database, so that a specific alignment algorithm—ideally including an additional pipeline configuration for that—can be applied. Another aspect of the "modified alignment functionality" refers to the fact that the alignment algorithms are adapted to be optimized for in-memory database use. In contrast to traditional algorithms, which access input and output files in the file system, modified alignment algorithms may also make use of the data stored or to be stored directly in the in-memory database system. As a result, media breaks are reduced, throughput is increased, and analytical queries can be performed on top of all data stored in the in-memory database without the need for extraction, transformation, and loading into a dedicated OLAP system as of today.

The term "CPU" refers to a central processing unit of a computer or a cluster of computers. Generally, a computer can have more than one CPU. In this case the computing system is called multiprocessing. Some microprocessors can contain multiple CPUs on a single chip, which are called multi-core processors. It is also possible to provide a distributed interconnected set of processors.

The platform layer refers to a computer-based architecture for integrating processing of genome sequencing data into the in-memory database. It has to be pointed out that according to the present invention all processing results and intermediate results are no longer stored as files in a file system, but are instead provided in the in-memory database system. Thus all operations, for example sort, merge etc., which are performed by dedicated tools on files, are replaced by native in-memory database transactions by means of operational (OLTP systems) and analytical (OLAP systems) transactions.

The in-memory database is based on utilization of main memory technology in combination with a column-oriented data structure, so that combined column and row store can work on the set of data. This in-memory technology is thus no longer based on disk storage mechanisms. Analytical as well as transactional systems are integrated and combined. According to an aspect of the present invention, OLTP queries can be performed on incoming data. Incoming data may comprise, in particular, sequencing data, (provided by the NGS machine) and annotation data (provided by the updater framework, which are integrated from all external registered distributed annotation sources or data bases), as well as other genomic data. The processing results according to the present invention, comprising intermediate and final results may be stored in either row- or column-oriented database format in the in-memory database system. The columnar database format supports OLAP queries so that OLAP operations benefit from an interactive response time behavior. Data stored in column-oriented database format may be updated on a regular basis by both incoming data and results, this being combined with the advantage that the in-memory database enables performance of OLAP queries on column-oriented data formats without any latency (i.e. in real time). As to the features and advantages of an in-memory database underlying the present invention, it is referred to patent application EP 2 040 180, describing details of an in-memory database.

The worker framework interacts with the in-memory database (in the following abbreviated as IMDB) and is an intermediate actor between different applications (application layer) and data (data layer). It specifies for incoming sequencing request required tasks and subtasks and its order comparable to a map reduce approach, known in the art. It also dispatches these tasks to computing resources, such as computing nodes, observes their status, and combines partial result sets to obtain the final result set.

The updater framework also interacts with the in-memory database and is an intermediate means between different applications (application layer) and data (data layer). It is the basis for combining international research results. It regularly checks Internet sources, such as public FTP servers or web pages, for updated and newly added annotations, e.g.

database exports or characteristic file formats, such as CSV, TSV, VCF, etc. New data is automatically downloaded and imported in the IMDB to extend the knowledge base. It also parses related literature sources, such as PubMed, and updates references in the database. Optionally, there also might be a selection of the set of external databases to be checked and/or the results may be selected to only import relevant findings into the in-memory database. Once new data was imported, it is available for real-time analysis of genome data without any latency. For example, selected research databases that are processed by the updater framework are: National Center for Biotechnology Information (NCBI), Sanger, University of California, Santa Cruz (UCSC), etc. Preferably, there might be implemented a selection process in order to select relevant research literature for the specific use case (for example special databases might be included and others might be neglected).

The processing pipeline will not be programmed in a fixed manner, but according to an aspect of the present invention will be graphically modeled, e.g. using common notations such as Business Process Model and Notation (BPMN). Thus, also different pipelines may be configured, for example implementing different alignment algorithms. These pipelines may be processed in parallel. This is a major performance enhancement due to parallel data processing. Furthermore, individual pipeline configurations guarantee comparability of results obtained by different research groups.

As the alignment processing step generates only few additional attributes for each read while the reads themselves are unchanged, the property of an in-memory column store database of allowing to add or modify single columns very fast without having to access the remaining columns represents a significant advantage over current implementations that store all information in flat text files mostly consisting of the replicated input information.

Typically aligning is based on dividing each read into non-overlapping seeds. However, it is also possible to use overlapping seeds.

According to an aspect of the invention alignment uses an early out heuristic in order to delimit future alignment processes to a fraction of genomic data.

According to an aspect of the invention, seeds are used for adapting the alignment algorithm, so that gaps are filled with a heuristic approach. This has the technical effect that a time and resource intensive alignment algorithm like Needleman Wunsch needs only to be applied seldom and only on a small fraction of the data.

According to an aspect of the invention, alignment is based on a double indexing, in that hits from each of two subsequent seeds in a reference genome are combined and stored in a separate smaller index structure, in case a configurable threshold for seed matches in these two subsequent seeds is exceeded. With other words: If two subsequent seeds in a reference genome (to be compared and aligned with the genomic sequence) will provide too many hits, said two subsequent seeds will be combined and stored in a separate index structure, which of course is significantly smaller as the other (first) index structure. In case two long hit lists are found in subsequence, it is possible to look up in said (second) index structure in order to get a significantly shorter hit list. This is due to the higher degree of selectivity of the longer seeds. As an advantage processing time as well as resources may be diminished.

Another aspect is to be seen in the flexibility to model pipeline configurations dynamically instead of having a predefined set of static pipeline configurations. For example, single or multiple alignment algorithms may be selected from a set of alignment algorithms and combined to improve accuracy of results, especially for rarely known genomic differences. Further, specific pipeline configurations may be selected and applied, for example, to provide a basis for comparing different genomic data sets on a homogenous foundation.

According to an aspect of the present invention a single or two-array index data structure is generated and stored in the in-memory database.

According to an aspect of the present invention an index data structure is replicated over local memory of processor sockets or over multiple nodes of the cluster in order to allow for on-the-fly read alignments on a massively parallel machine.

A major aspect of present invention is to be seen in that index structures as well as alignment algorithms are optimized with respect to cache misses.

Preferred embodiments of the method and the system according to present invention are described below. In this respect it has to be noted that, generally, the invention also might be implemented in hardware or in hardware modules combined with software modules. The hardware modules are then adapted to perform the functionality of the steps of the method, described above. Accordingly, it is also possible to have a combination of hardware and software modules. The modules are preferably integrated into an existing bio-technological or medical environment, for example a sequencing environment. The features, alternative embodiments and advantages which will be or have been described with respect to the method may also be applied to the system as well by means of hardware modules, which are adapted with the functionality of the respective method step and vice versa.

BRIEF DESCRIPTION OF THE DRAWINGS

The invention will now be described with reference to the drawings wherein:

FIG. 4 shows extensions to a Needleman-Wunsch alignment algorithm;

DESCRIPTION OF THE PREFERRED
EMBODIMENTS OF THE INVENTION

Figure 6:
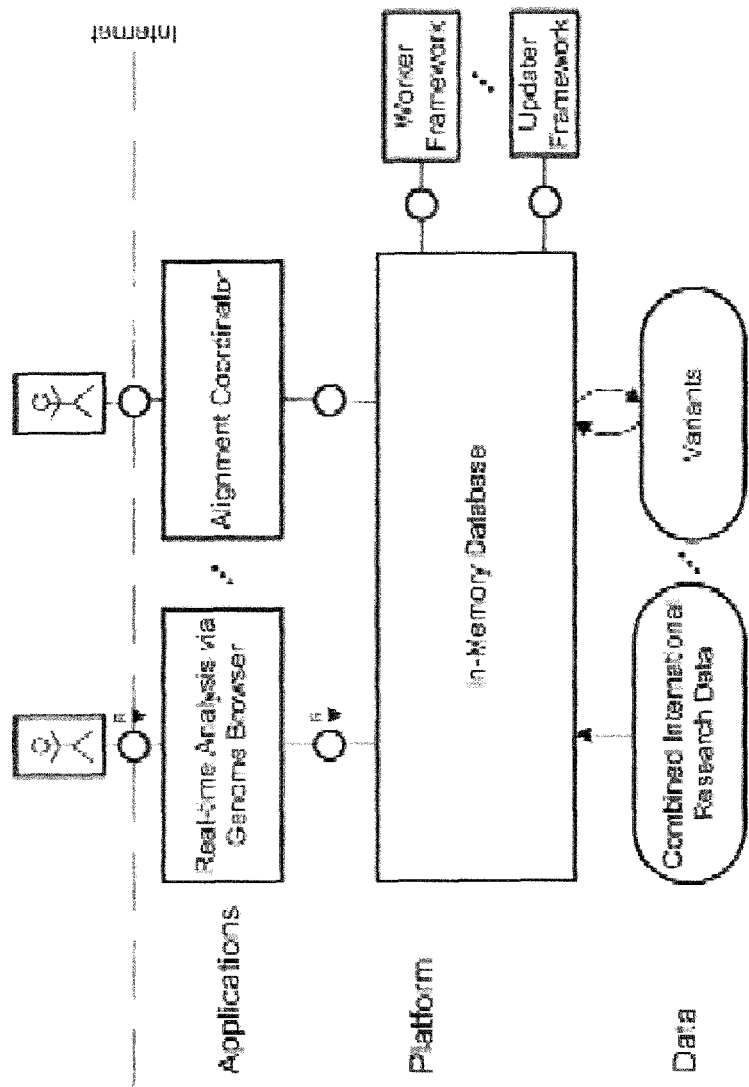
FIG. 6 illustrates a schematic overview of the system architecture.

FIG. 6 depicts the data, platform, and applications layers of the system architecture with the IMDB as the heart piece enabling real-time analysis modeled as a Fundamental Modeling Concepts (FMC) block diagram. In the platform layer the in-memory database IMDB combines data from international research databases and exposes real-time analysis capabilities to the cloud applications. As can be seen in FIG.

6 the in-memory database IMDB in the core computer instance and interacts with external databases (e.g. annotation databases) and with the worker and updater frameworks for data processing. On a higher level different applications are located for real-time analysis and genome browsing as well as for alignment by means of an alignment coordinator.

Figure 5:
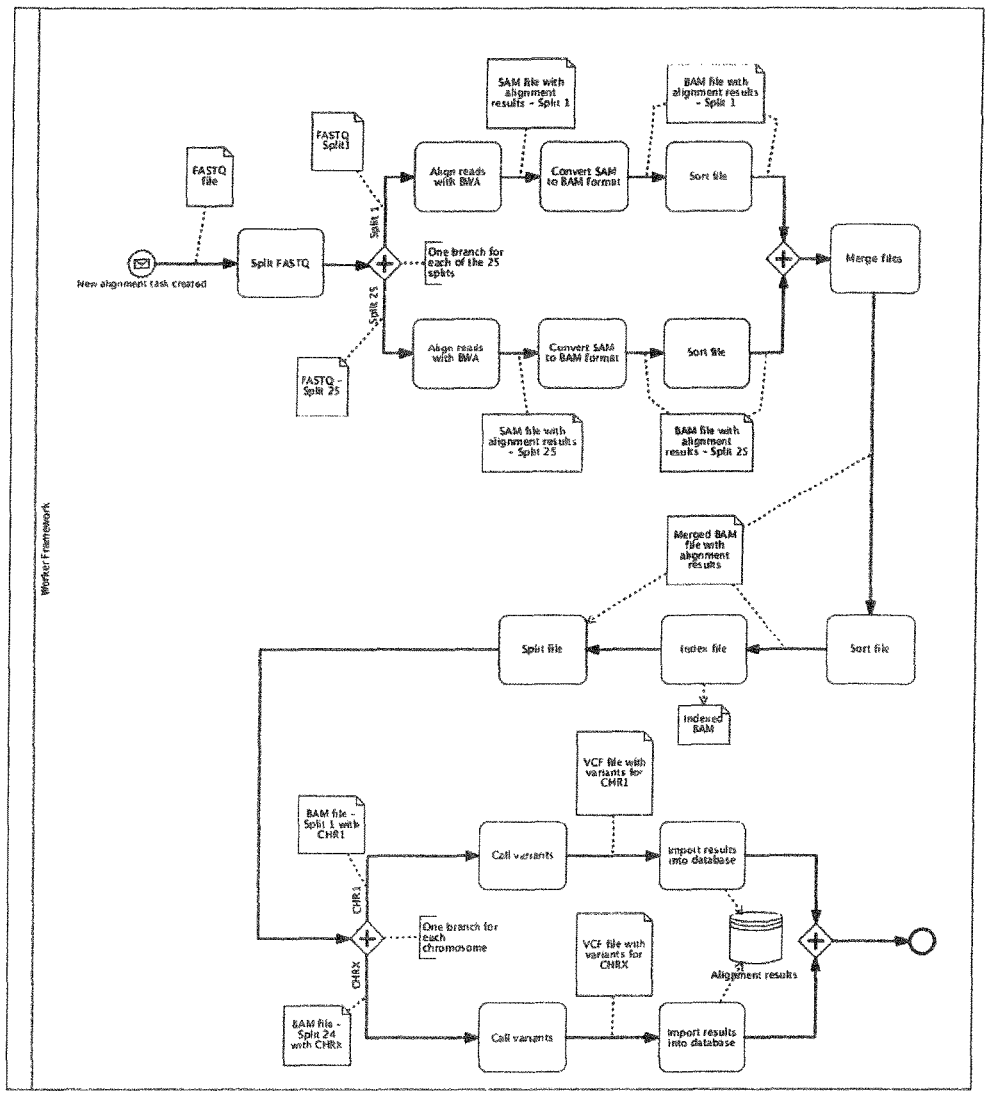
FIG. 5 shows a schematic overview of the system pipeline according to a preferred embodiment of the present invention.

FIG. 5 depicts a typical genome-processing pipeline as of today modeled as Business Process Modeling and Notation (BPMN). FIG. 5 shows a genome data processing pipeline as integrated in this research prototype modeled in BPMN. The input FASTQ file is split in up to 25 chunks for parallel data processing on a 1,000 core cluster. Firstly, the specific alignment algorithm is called in parallel, here BWA, and conversion steps are performed until a combined BAM files is created. Secondly, the BAM file is split into individual chunks, one per chromosome, and variant calling is processed in parallel. The results are imported into the IMDB to enable real-time analysis of the results.

Figure 7:
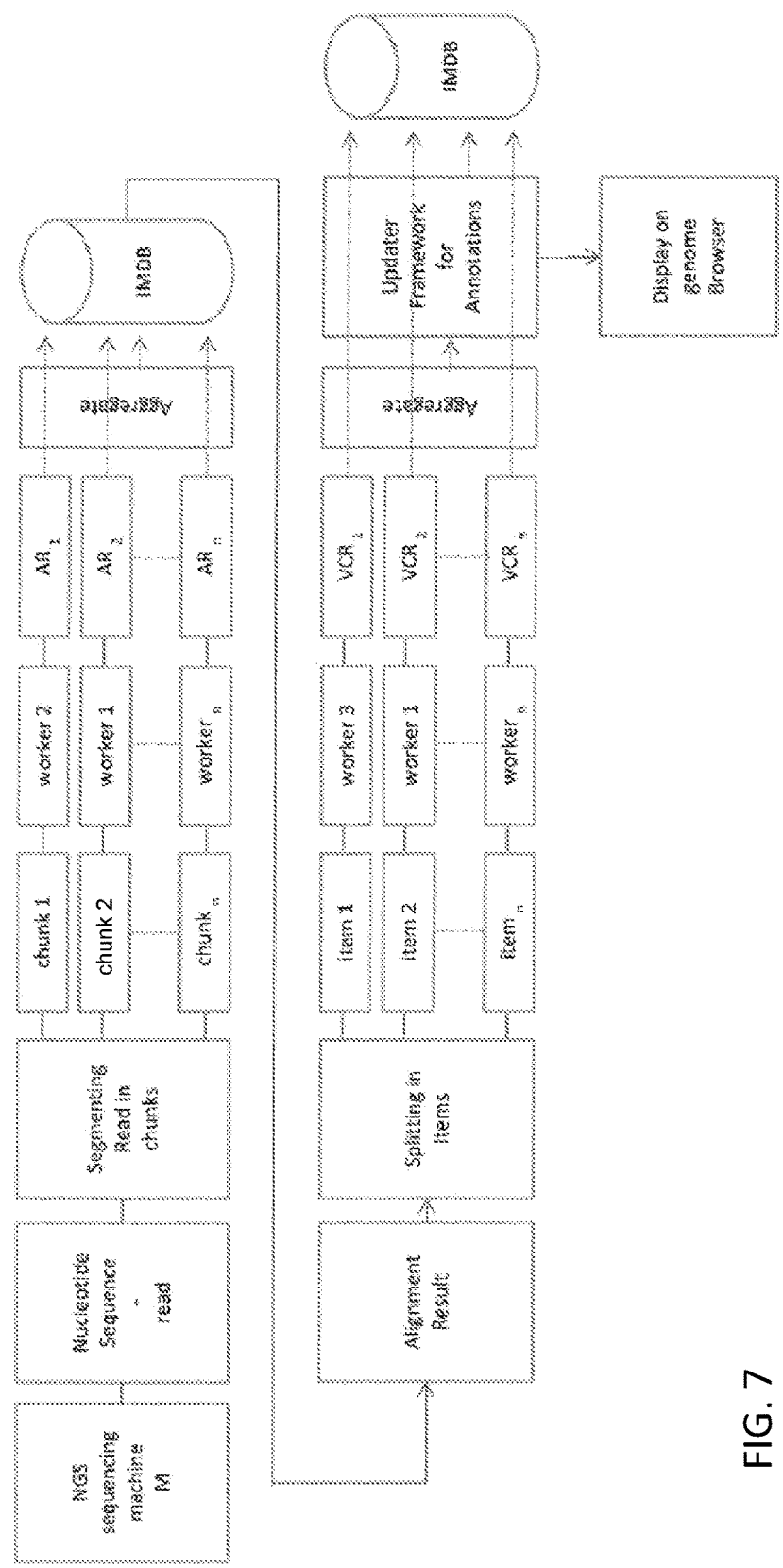
FIG. 7 illustrates processing nodes according to a preferred embodiment of present invention.

FIG. 7 illustrates the overall in memory based architecture, consisting of OLAP- and OLTP-transactions in order to provide genomic data processing. As can be seen in FIG. 7, a nucleotide sequence is provided by a sequencer machine M, which is depicted in FIG. 7 on the left hand side. According to the pipeline a set of reads is provided. Each read is segmented in a configurable amount of chunks, particularly in 25 chunks, wherein each of the chunks is associated or allocated to a worker of the node cluster. As can be seen in FIG. 7, the allocation of workers as processing devices to chunks is also dynamically configurable, so that in the example here, chunk 1 is assigned to worker 2 and chunk 2 to worker 1, possibly because chunk 1 is most demanding in processing power and worker 2 has at this moment most degree of spare resources. Each of the workers then provides a partial alignment $AR_1, AR_2, \ldots AR_n$ result by executing a configurable alignment algorithm, which each is stored in the IMDB database. It has to be noted that each of the chunks may be processed with different alignment algorithms (if the user wishes to do so). Accordingly, it is also possible to use different alignment algorithms for different reads. A major aspect is also to be seen in that alignment starts while sequencing is still computed or processed. Thus this method may be implemented as soon as the first sequence result is available. After all partial alignment results ARi are aggregated, the partial result $AR_i$ as well as the overall aggregates result is stored in the IMDB database.

After this several database transactions are to be executed and an overall alignment result is provided, which then is also split into items for parallel processing, by means of variant calling algorithms which again might be configured for the respective use case for the pipeline. Each worker provides an intermediate result of the variant calling $VCR_1$, $VCR_2, \ldots VCR_n$. These partial results $VCR_i$ are stored in the IMDB database and are aggregated to build an overall result which is also stored in the IMDB database. Concurrently, the result may be displayed on the user interface UI.

The integration of DNA in course of personalized medicine consists of the two major steps DNA sequencing and analysis of genome data. DNA sequencing spans the biological preparation of samples, e.g. blood or tissue, and its sequencing using a NGS device. The analysis of genome data is an IT-driven step processing FASTQ files from NGS devices, which includes alignment, variant calling, and the analysis of the results.

Alignment is the reconstruction of the specific full genome by combining the acquired read sequences with a selected reference genome.

Variant calling detects anomalies in the reconstructed genome and checks whether these are possible variants, e.g. manifestation of certain alleles. The last and most time-intensive step is the analysis of all results from the variant calling and its interpretation using worldwide annotation databases. The genome browser of the present application addresses the ad-hoc analysis of the results without the need for time-consuming manual Internet searches.

Parallel Data Processing

This application discloses a dedicated data processing framework in Python providing a set of workers. Each computing node is equipped with a dedicated worker. They process complex tasks, i.e. tasks that either include multiple jobs or long-running, non-interactive batch processes, such as the sequence alignment of reads for a whole genome. Non-complex, interactive tasks are directly executed by the web service and do not involve the worker framework. Complex tasks are split in atomic portion of work by the worker framework for parallel data processing. Atomic jobs can be executed in a distributed manner. Once a worker is available, it fetches the next job from the job queue and executes it automatically.

The synchronization of jobs and worker is performed via a job database table, which contains new, currently processed, and finished jobs as well as their status, e.g. new, in progress, finished, failed, etc. All workers directly access the jobs table via their local database instance and self-assign the next appropriate task. Concurrency control is guaranteed by the IMDB, i.e. primary keys on the attributes TASK-ID, JOB-ID, and STATUS guarantee that only a single worker can change the task's STATUS attribute from NEW to IN PROGRESS. Just after the updated status is confirmed by the database system, the worker starts the job processing.

The job execution is handled via modular Python scripts, which are loaded on demand by the worker framework. The worker module selects unassigned jobs from the queue. Job dependencies and synchronization of a specific subset of jobs is self-coordinated by dedicated jobs evaluating the content of the job database table.

All Python job modules inherit from the super module Job, which provides generic methods, such as status updates or logging of errors. The code executed by a job is located within the respective job module, e.g. alignment of raw DNA reads or imports of CSV files into the database.

This invention enables the use of individual tools and scripts per job. As a result, it is possible to integrate existing tools, e.g. samtools, bcftools, vcftools, as well as highly optimized in-memory specific tools into the pipeline. The application successfully integrated a variety of defacto standard alignment algorithms in the pipelines, such as Burrows-Wheeler Aligner (BWA), Bowtie, Bowtie2, SNAP, etc. . . . .

Sequence Alignment and Variant Calling

The inputs for alignment tasks are FASTQ files containing thousands or millions of raw DNA reads or snippets. FASTQ files are generated by the NGS device in a time-intensive process. Instead of waiting for a single huge FASTQ file, the start will processing as soon as possible, i.e. once FASTQ chunks, e.g. with a file size of 256 MB, are generated by the NGS device. As a result, the data processing already starts while the sequencing run is still in progress. The results of the variant calling are stored in a task specific database table compatible to the Variant Calling Format (VCF).

FIG. 5 depicts a genome data processing pipeline with the BWA alignment algorithm modeled as BPMN. Although those steps have a similar overall functionality as state of the art pipelines, all processing steps and tools are transferred to IMDB. Thus, all intermediate results are stored in the database and selected operations are replaced by native database operations of the IMDB. The present system, thus, refers to an integration platform for existing tools and pipelines and a development platform for highly optimized algorithms, e.g., HANA Alignment. The FMC diagram below shows the general procedure for a sequence alignment. Steps 2-4 take place for all splits of the FASTQ file on several nodes. Steps 5-8 can only be performed on one node, whilst after the splitting, steps 9-10 again are executed on at most 24 different nodes:

1. FASTQ files are split in multiple chunks to enable parallel processing on several nodes,
2. Specific alignment algorithm reconstructs genome in SAM format. The alignment algorithm may be selected or chosen (BWA; Bowtie etc.)
3. SAM file is converted to a binary representation, i.e., BAM format, for subsequent variant calling;
4. BAM file is sorted as a preparing step for step 5 (for merging);
5. BAM files are merged into a single BAM file;
6. Cumulated BAM file is sorted for indexing;
7. BAM file is indexed;
8. BAM file is split into individual chunks per chromosome (24 splits) for parallel processing;
9. Variant calling is performed, e.g. samtools, and VCF files are created, and
10. VCF files are merged and the cumulated result set is imported into the database IMDB for real-time analysis.

In the pipeline optimized for the IMDB technology the processing steps for sort, merge, and indexing are not performed by specific tools. These steps are directly executed by the IMDB without the need to create intermediate files in the file system.

One main advantage of the present invention is that by using careful algorithm engineering it is possible, despite all these hindrances, to solve the alignment problem in a few minutes on a moderately powerful workstation. This translates to almost negligible computational cost. The underlying reason for this somewhat surprising result is threefold. On the one hand, the invention can profit from Moore's law twice. The algorithm is easy to parallelize and can thus utilize modern multicore processors. It profits even more from fallen RAM prices that allow it to use fast and simple yet memory intensive data structures. On the other hand it orchestrates a long list of simple yet effective algorithmic techniques to gain performance. Perhaps the most fundamental aspect here is that it exploits that error rates in reads are sufficiently low that the application can take a number of "shortcuts." For most reads, it suffices to check for exact matches of non-overlapping substrings (seeds) to the reference genome and only have to inspect those candidate positions more closely that have several of these exact matches. The application can even ignore substrings that are too frequent in the reference genome. For the small set of remaining unaligned reads, one can afford more (computational) expensive searches. The actual alignment at the candidate positions can also profit from low error rates, which make very simple forms of bit parallel matching practical.

Having more or less solved the alignment problem, the grand challenge becomes the overall workflow of sequencing, archiving, and processing huge amounts of sequenced genomes. Based on a HANA technology, some specialized high performance algorithms can be implemented within the data base server where tailored algorithms can directly interact with the data. As data transfer and conversion are not required, this approach is superior to algorithms running on top of a data base. The alignment algorithm is a good example for such an implementation. It already profits from this architecture by processing a stream of reads on the fly, thus requiring main memory almost exclusively for the index on the reference genome which is much smaller than the overall volume of data read.

Previous Work

Alignment of short nucleotide sequences ("reads") against a reference genome has been subject to intensive study. There exists a variety of algorithms, some of the most popular ones being BWA-SW [see. Li, H., Durbin, R.: Fast and accurate long-read alignment with Burrows-Wheeler transform. Bioinformatics (Oxford, England) 26(5), 589-95 (March 2010)], SOAP2 [see: Li, R., Yu, C., Li, Y., Lam, T. W., Yiu, S. M., Kristiansen, K., Wang, J.: SOAP2: an improved ultrafast tool for short read alignment. Bioinformatics (Oxford, England) 25(15), 1966-7 (August 2009)], Bowtie 2 [see: Langmead, B., Salzberg, S. L.: Fast gapped-read alignment with Bowtie 2. Nature methods 9(4), 357-9 (April 2012)], SNAP [see: Zaharia, M., Bolosky, W. J., Curtis, K., Fox, A., Patterson, D., Shenker, S., Stoica, I., Karp, R. M., Sittler, T.: Faster and More Accurate Sequence Alignment with SNAP (November 2011)], SMALT and Masai [see: Siragusa, E., Weese, D., Reinert, K.: Fast and sensitive read mapping with approximate seeds and multiple backtracking. CoRR abs/1208.4238 (2012)]. A recent overview can be found in [Li, H., Homer, N.: A survey of sequence alignment algorithms for next-generation sequencing. Briefings in Bioinformatics 11(5), 473-483 (2010)].

Since reads contain slight differences to the reference genome and sequencing errors, every alignment algorithm needs to be tolerant to these differences. There are two basic approaches commonly used to find the best matching position of a read in the reference genome: backtracking and seeding. Backtracking tries several modifications of the input read and constantly checks if this modification is found in the reference genome. As the number of possible modifications is quite high and increases with the length of the read, the possible search space becomes too large to be completely covered by the algorithm. Therefore intelligent heuristics trying to follow the most promising paths and constraints on the number or type of modifications are commonly applied. Seeding based algorithms try to find a short sub-sequence of the read (seed) in the reference genome without any error tolerance. If such a sub-sequence exists, error tolerant extension algorithms try to match the rest of the read to the reference.

BWA-SW, SOAP2 and Bowtie 2 rely on FM indexes [Ferragina, P., Manzini, G.: Opportunistic data structures with applications. In: Proceedings 41st Annual Symposium on Foundations of Computer Science. pp. 390-398. IEEE Comput. Soc (2000)] while SNAP and SMALT use hash table based indexes.

FM index based algorithms are very memory efficient compared to hash table based algorithms even if the index is uncompressed. They are however very prone to cache misses as plenty of lookups against random memory positions have to be carried out. Especially algorithms using backtracking for error tolerant alignment (e.g. BWA-SW & SOAP2) produce many cache misses because several possible alternatives with errors have to be taken into account. This can become a severe performance bottleneck for long hashes. Hash table based implementations with long hash lengths tend to require a lot of memory (39 GB in case of SNAP) but avoid cache misses much better and therefore usually perform faster.

Masai [Siragusa, E., Weese, D., Reinert, K.: Fast and sensitive read mapping with approximate seeds and multiple backtracking. CoRR abs/1208.4238 (2012)] combines both approaches by using backtracking on seeds that are allowed to contain a small number of errors. This makes it both accurate and fast. However, Masai needs a lot of memory since it needs an enhanced suffix array for the reference genome plus a radix-tree data structure for the seeds.

The Alignment Algorithm according to present invention uses the basic idea of building an index data structure to allow finding all substrings of length S=16 (seed length) in the reference genome quickly. The data structure is quite simple: For all $2^{32}$ substrings of length 16, a list of all positions in the reference genome where this substring occurs is stored—there is no hashing and no suffix array.

From a hardware point of view, this approach works well because processing these lists can be done by just scanning arrays which is much more cache efficient than working with more sophisticated data structures. Also it is noted that this approach resembles the inverted index data structures used in information retrieval.

Reads are processed independently and thus in a seemingly parallel manner. The only care that has to be taken is that synchronization overhead for parallel reading and writing of data does not become a bottleneck. This can be achieved by processing entire blocks of reads at once. This application employs techniques from search engines to quickly find promising candidate positions for alignment.

Index Structure

The index consists of two parts: an array e of $4^{16}$ entry points and an array m of matching positions in the reference genome (reference position). m[e[s], ..., e[s+1]−1] stores those positions in the reference genome matching seed s.

This structure can be computed in linear time by iterating over all reference genome positions and counting the number of times each seed appears. This information can be stored directly in e without requiring any additional memory. In the next step these counts are aggregated by adding the counts for all the seeds that are smaller. This already provides the correct entry points to the matching position list, which can then straightforwardly be filled by iterating once again over the whole reference genome and storing the values this time. This step can also be computed without any memory overhead as the entry point index can be used to store the next writing position for each seed. For that purpose every time a seed is found, its entry point is increased by one such that it can be used as a write offset for the next time. After the whole genome has been processed, each seed entry point contains the value of the next seed and the data structure just needs to be shifted back by one seed to recover its original value.

The index construction is therefore simply a memory efficient implementation of a counting sort. Due to the large number of counts, the algorithm causes a lot of cache misses and is also not so easy to parallelize. The direct parallelization is somewhat simplistic yet quite effective for a moderate number of cores: each core is responsible only for a subinterval of the counts. It scans the entire reference genome but only increments counts assigned to it.

At the expense of higher space consumption, there can be at the same time a more scalable parallelization and a significant reduction of the cache faults by using a parallel cache-optimized sorting algorithm. The p resent invention is based on the highly tuned radix sort described in [Sanders, P., Wassenberg, J.: Engineering a multi-core radix sort. In: Euro-Par. LNCS, vol. 6853, pp. 160-169]. Note that it suffices to sort the seeds as the positions are already sorted by construction and the sort is stable.

The positions in the index refer to a concatenated version of all chromosomes in the reference genome for reasons of performance and simplicity. This allows to get all the relevant positions in one call, which keeps the number of cache misses low and avoids having to merge multiple lists. Thanks to a very fast index structure, there is basically no overhead. The corresponding reference chromosome for a match can be found very efficiently using another index structure. This chromosome index is based on simple bit shifting and integer comparisons. First, all chromosomes are concatenated and the offset $o_j$ (for chromosome j) for each chromosome is saved so that it can later be subtracted. Now the minimum number k of most significant bits is computed such that the beginnings of two chromosomes never have the same values for their k most significant bits. A lookup table bin of size $2^k$ is built in which bin i represents all positions in the reference genome with most significant bits i and stores the id of the rightmost chromosome that overlaps bin i. A lookup for position x computes:

j=bin [x:1»(32−k)] and then checks whether $o_j \le x$. If so, j is the correct chromosome id. Otherwise, the correct id is j−1.

For the human genome, only 7 bits are required which yields 128 bins. With 64 bit wide pointers the structure is only one kByte large and comfortably fits into the L1 cache.

Finding Candidate Matches

Each read is divided into R/S non-overlapping seeds, where R is the read length and S the seed length. Accordingly, some non-aligned size S matches are missed, but this approach also saves a factor Sin running time over a brute force approach. By querying each seed in the seed index a sorted list of positions where this seed matches (hits) is obtained. As most seeds have multiple hits, the possible search space grows with each seed of the read. This becomes even worse as some very common seeds might have thousands to hundreds of thousands of hits. To avoid this, the application attempts to combine the hits from each seed (forming a match) and to use only the matches with most hits as they are most likely to have the highest overlap to the reference genome.

To combine the hits to matches and find the most promising matches, the algorithm iterates over all seeds. Previous matches are stored in a list ordered by reference position and combined with the list of hits of the current seed. Since both lists are sorted, this combination operation is basically a generalized form of merging and closely related to the operations performed in search engines when combining hit lists for several key words.

The decision is based on an optimistic computation of the score such a match can ideally achieve. In this respect it is referred to FIG. 1. The scoring uses penalties of $p_{\ne}2$ for mismatches, $p_{\pm}=3$ for insertion/deletions and no penalty $p_{=}0$ for matches. The penalties are based on negative logarithmic probabilities as these can simply be added to get the total penalty which would be equivalent to the product of all probabilities. A penalty of 2 corresponds to a probability of $10^{-2}=1\%$ and 3 to $10^{-3}=0.1\%$. The higher the penalty score, the worse a match is. Seeds with more than 16 hits are ignored but optimistically counted as a match and not getting a mismatch penalty to avoid growth of the search space beyond reasonable sizes. The score for the first matching seed is $$s \leftarrow i \cdot p_{\ne}$$

where i is the index of the seed in the read starting from 0. This simply means that the i seeds before did not match while the current seed with index i matches. Furthermore, the first match determines the reference position of the match $$r \leftarrow r_j - i \cdot S$$

The subsequent scores are based on the position of the last hit $r_i$, the one of the current hit $r_j$ and their distance in base pairs $d:=(j-i-1)\cdot S$ on the read $$s \leftarrow s + |r_j - r_i - d| \cdot p_\pm + (j - i - 1 - |r_j - r_i|) \cdot p_\ne$$

which is composed of the misplacement of $r_j$ from the expected position $r_i + d$ times the insertion/deletion penalty plus the minimum number of mismatches required to explain the number of missed seeds in between times the mismatch penalty. The latter term can be explained by a simple example. If seed j had a misplacement of 2 from its expected position there had to be at least two insertions or deletions. If, however, three seeds were missed in between then there needed to be at least another mismatch to explain why the three seeds were missed.

Figure 1:
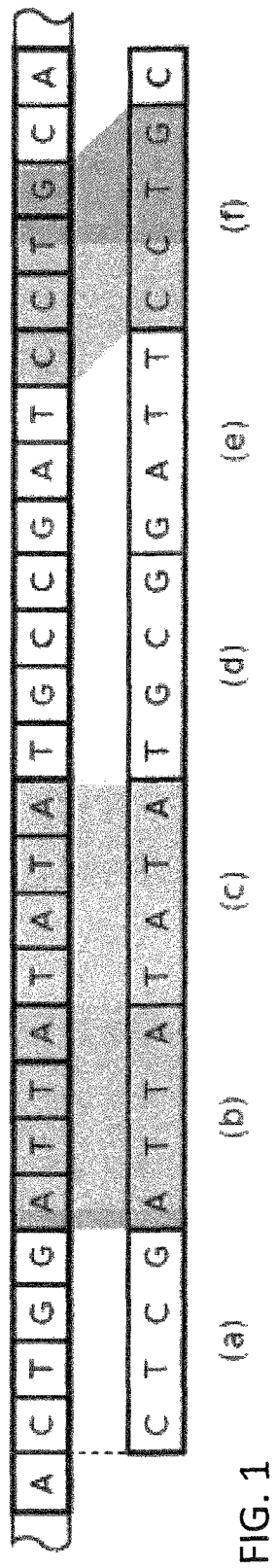
FIG. 1 illustrates a seed scoring according to a preferred embodiment of the present invention using the nucleotide sequences having SEQ ID NO:1 and SEQ ID NO:2.

FIG. 1 shows a seed scoring, wherein the numerals a to f represent the following scenarios/events:
(a) "No match is found so ignore this seed until further information is available",
b) "first match found. Count all matches before as mismatches unless they were ignored due to too many results. Assign reference position (dashed line) to assumed start."
(c) "Too many results so seed is optimistically being assumed to match at the right position."
(d) "No match found."
(e) "Insertions shifts following seeds by one."
(f) "Match found. As two seeds have been missed there need to be at least two mismatches. The shift indicates at least one insertion which weighs stronger than a mismatch. Optimistically therefore assume one mismatch and one deletion."

Figure 2:
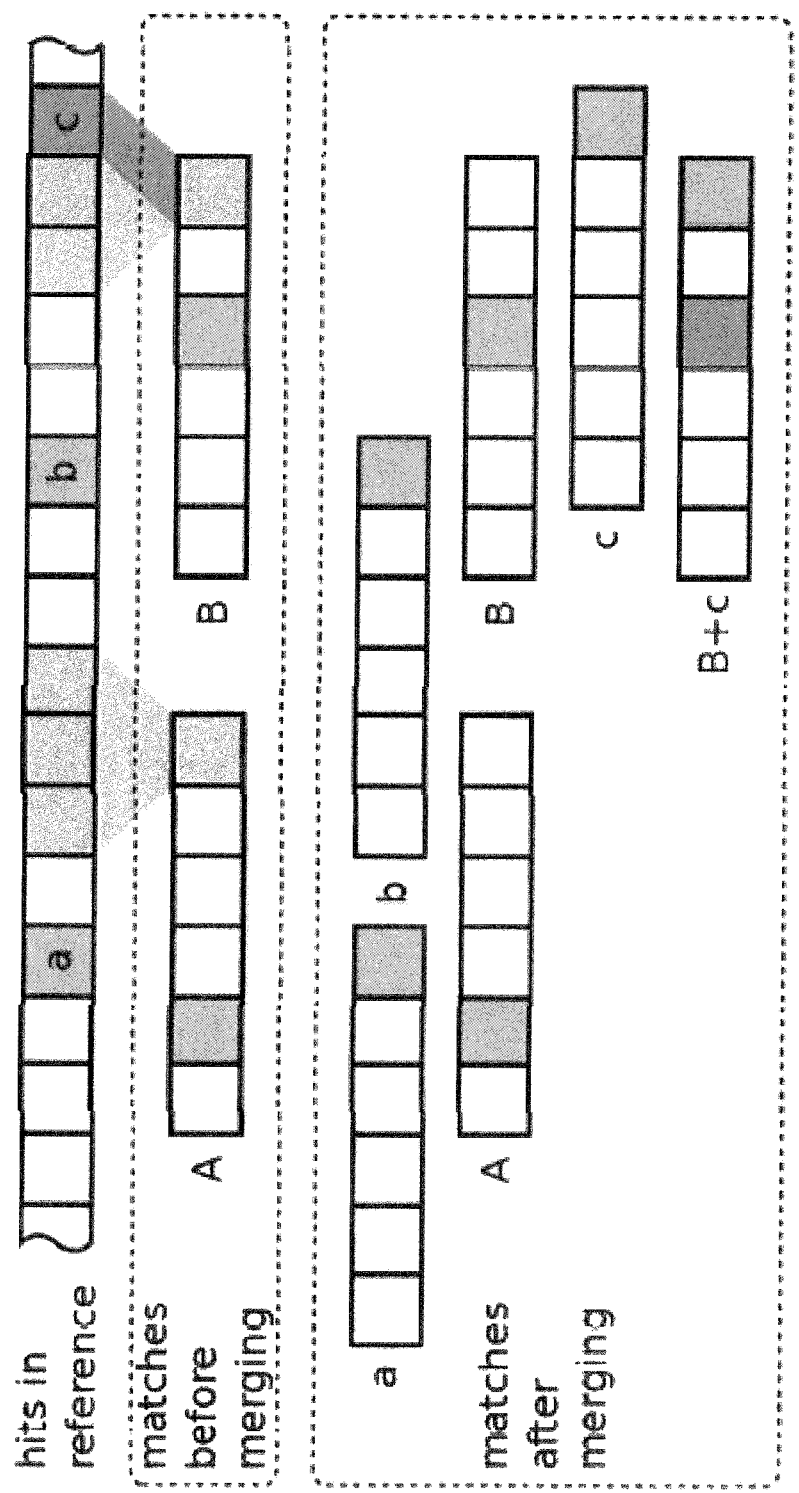
FIG. 2 is an exemplary illustration of merging match lists with new hits.

FIG. 2 represents merging match lists with new hits. All hits (lower case letters in the reference sequence) for the current seed (last seed of the read in this example) are compared to the region of each previous match that would yield a score below a given threshold. If both overlap then a combined match is added. In any case the previous matches are copied if the optimistic score is still below the threshold assuming a mismatch there. Similarly the new hit is added assuming that all seeds before were mismatches. Previously ignored lists are stored within a reference genome match so these seeds are excluded from the score computation. Since the lists are always sorted by reference position they can be compared without much effort as possibly matching lists are spatially close.

In principle the scores for all match/hit combinations need to be computed and all combinations that are below the given score threshold should be kept while the other ones are discarded. Since the application can exclude most of these combinations by the fact that their reference positions are too far apart and both lists are ordered, this invention can simultaneously iterate over both lists and only compute the scores within a small window as all matches that are more far away will for sure score worse due to the high insertion-deletion penalty (see also FIG. 2). Since both lists are scanned only once and the windows are very small, this method is very cache efficient as accesses are not random but local. Basically all list accesses should be within the L1 cache and pre-fetching can be applied optimally.

In the end the best scoring match is determined and all matches that have less than half of the maximum score are pruned. If there has been at most one matching seed further processing is done to identify the best candidates out of these (see below).

Seed Extension

Figure 3:
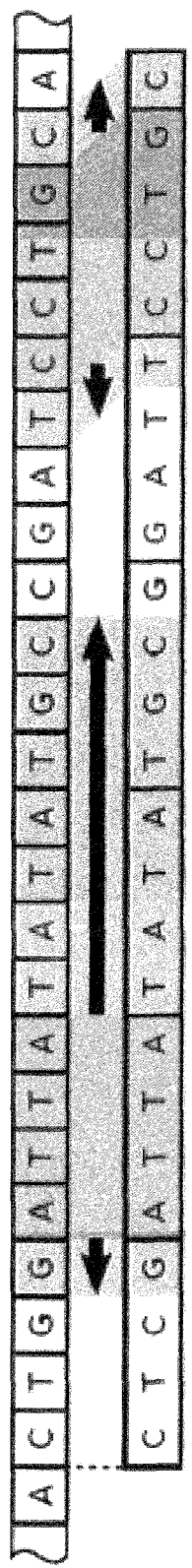
FIG. 3 illustrates seed extension according to a preferred embodiment of the present invention using the nucleotide sequences having SEQ ID NO:1 and SEQ ID NO:2.

FIG. 3 illustrates a seed extension. Starting from the matches to try to extend the seed as much as possible and end up with two remaining gaps.

After the initial seeding is done, the most promising candidates with respect to the score for each read are processed further. The system and the method according to this application also perform some initial filtering of the matches to limit the possible score and minimum number of matching seeds.

In the first stage, the seeds are extended as much as possible using bit parallelism because on a 64 bit architecture, up to 32 base pairs can be compared in one operation using XOR. Then the matching positions can be counted using count leading/trailing zeros operations on modern CPUs. After dividing the result by two, this immediately yields the number of base pairs by which the match can be extended.

Simple Gaps

The alignment information including deviations from the reference sequence can be reconstructed by iterating over the extended seeds starting from the leftmost reference position. This creates a list of segments alternating between matching regions (extended seeds) and the gaps in between them. While the extended seeds describe perfectly matching regions that can easily be processed, the gaps might contain complex deviations from the reference sequence.

Thanks to the low error rate, most gaps end up in one of the following four classes:

1. Empty Gaps. Both the gap on the read and on the reference genome are zero bases long. This can happen if the gap consisted of an ignored seed due to the high amount of matching positions.

2. Single substitutions. Both the gap size on the read and the reference genome are one base long. The gap must therefore represent the substitution of a single base.

3. Insertions. The gap size on the reference genome is zero but non-zero in the read. This means that all bases on the read must have been inserted.

4. Deletions. The gap size on the reference genome is non-zero but zero in the read. This means that all bases must have been deleted from the reference genome.

The alignments for these simple gaps are easy to compute and do not require any additional logic.

Complex Gaps and Loose Ends

If the matches are not extending all the way to the ends of the read, then the loose end needs to be treated in a special way. The same applies to gaps that did not match the criteria above and might require complex combinations of matches, substitutions, insertions and deletions.

For this kind of problem, two established algorithms are available: Needleman-Wunsch [Needleman, S. B., Wunsch, C. D.: A general method applicable to the search for similarities in the amino acid sequence of two proteins. Journal of molecular biology 48(3), 443-53 (March 1970)] and Smith-Waterman [Smith, T. F., Waterman, M. S.: Identification of common molecular subsequences. Journal of molecular biology]. While the first one is designed for global alignments and therefore perfectly applies to gaps, the second one is designed for local alignments. As the loose ends require some flexibility on one end but not on the other, the application uses a modified Smith-Waterman algorithm for this purpose.

Compared to Needleman-Wunsch the Smith-Waterman algorithm applies several modifications as listed in FIG. 4. The effect of these modifications is that local alignments are detected. These are short matching sub-sequences within the two nucleotide sequences. In this case, however, it is desired to provide this freedom on one end only and not allow clipping the read but only the reference. Clipping the read might be desired in some situations, but it is not the general case, so clipping the read is made optional. Depending on the boundary conditions, some parts of the Smith-Waterman modifications need to be enabled (see the table in FIG. 4). In considerations, the rows correspond to the individual bases in the read while the columns represent the bases in the reference.

The table in FIG. 4 illustrates extensions to the Needleman-Wunsch algorithm. Depending on the type of gap/end and the settings, the Needleman-Wunsch algorithm is modified. Rows correspond to read bases and columns to reference bases. Clipping turns on more features and makes this algorithm close to the Smith-Waterman algorithm. The extreme case of not open on any end and no clipping yields the regular Needleman-Wunsch algorithm while the opposite (open on both ends with clipping) yields Smith-Waterman.

Handling Unmatched Reads

Most reads that can be matched to the reference genome at all can be matched with the fast methods described above. This is an application of the engineering principle "make the common case fast." For the few remaining reads the application can afford more expensive methods. In particular, one can use all substrings of length S as seeds. What remains are mostly reads that either have a fairly high error rate and thus may be less useful than the other reads, or reads that do not come from the reference genome at all. Therefore, the current implementation stops here.

However, the former reads might still have some utility. Matching them requires methods that build on shorter exact matches. If enough space is available and the index construction time is not an obstacle, the application can use any of the existing backtracking based read aligners. This application will keep much of its speed advantage because the expensive method will only be applied to a small fraction of the reads. However, there is also a cheap extension of the instant method that will extract the most useful information out of the unmatched reads: In most cases a user does not care for additional reads mapped to pieces of the genome that are already well covered by other reads. But there will always be a small fraction of the genome that is not well covered and here, mapping some of the remaining reads will be very valuable. This is particularly crucial where the insufficiently covered region is not there by chance, but due to a large scale mutation, which can be biologically highly relevant. For this purpose the method and system according to this application extract the pieces of the reference genome which are insufficiently covered (together with a window of size R) and build a new index structure with seed length $S'<S$ for them. Now, the application ca n repeat the algorithm with the unmapped reads (and perhaps those that have a low mapping score so far). This will again be fast since the hit lists will be much shorter for the reduced reference genome.

As a comparison of the performance of the algorithm compared to other state-of-the-art alignment algorithms the invention ran BWA-SW and Bowtie 2 on the same data and compared the alignment rates and throughputs of reads per millisecond.

In one embodiment, all measurements were performed on a Machine with 4 Intel Xeon E-7560 hexa-core processors clocked at 2.67 GHz. The machine had 504 GByte of RAM. However, all the codes would also work with 64 GByte—the application used the remaining memory to do all I/O from RAM disk in order to measure only the performance of the algorithm rather than details of the I/O hardware.

Discussion

The read alignment algorithm is so fast that it causes only negligible computational cost of a few cents. This means that even if laboratory technology for sequencing keeps getting cheaper at a faster rate than Moore's law, read alignment will not become a bottleneck. Although this application has been tested by performing experiments for the currently important case of reads of length around 100, the present method seems fairly independent of the read length—in contrast to several backtracking based methods that only work well for very short reads. Furthermore, the present method will work well as long as the beginning of the read has a low error rate which seems to be the case for many sequencing technologies.

The index construction time and memory footprint of the present method is also much faster than previous methods, in particular than those based on advanced data structures such as suffix arrays/Burrows-Wheeler transform. This makes it much easier to change the reference genome, which can be important for non-human genomes or when the user wants to use the genome of a relative as a reference genome.

If desired, the performance of alignment algorithms can be further improved exploiting all three approaches: RAM, parallelism, and algorithmic improvements. For example, with even more RAM, this invention can replace the two-array index data structure with a single array of size B buckets where B is big enough to fit at least one cache line. Now the first B−1 hits for seed i are stored in bucket i. The B-th entry can be used to refer to an overflow area or an empty bucket. This way, one only incurs a single cache miss before being able to access the first B−1 hits.

To allow more scalable parallelism, the application can once more use more RAM by replicating the index data structure over the local memory of the processor sockets or over multiple nodes of a cluster. In principle, this would allow "instantaneous" read alignment on a massively parallel machine. Hypothetically assuming equally fast laboratory equipment and further processing, this approach would, for example, allow to immediately analyze tissue samples of a tumor during an operation and to decide how to treat the tumor.

Opportunities for algorithmic improvement include building index data structures on top of the long hit lists to allow merging them with short lists in time proportional to the length of the short list.

Finally, it should be pointed out that the description of the example embodiments are not to be understood as restrictive in terms of a particular physical implementation of the invention. In particular, it is obvious to a person skilled in the relevant art that embodiments of the invention can be implemented partially or completely in software and in a form distributed over a plurality of physical products—particularly including computer program products.

Further, any of the aforementioned methods may be embodied in the form of a program. The program may be stored on a computer readable media and is adapted to perform any one of the aforementioned methods when run on a computer device (a device, node, worker or network thereof including at least one processor core). Thus, the storage medium or computer readable medium is adapted to store information and is adapted to interact with a data processing facility or computer device to perform the method of any of the above mentioned embodiments Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-based system for processing nucleotide sequence data provided as reads, the computer-based system comprising:
   an interface configured to import the nucleotide sequence data from a sequencer machine (M);
   an in-memory database (IMDB) configured to store the nucleotide sequence data in a two-array index data structure and to integrate a plurality of alignment algorithms, the two-array index data structure including an array of entry points and an array of matching positions in a reference genome;
   a platform layer configured to hold process logic, the platform layer comprising:
   a worker framework with a plurality of workers, each worker running on a node of a cluster and the plurality of workers being assigned to chunks depending on available processing power and configured to process in parallel, wherein all results and intermediate results are stored in the two-array index data structure in the IMDB, and
   an alignment coordinator configured to:
   provide the IMDB with a modified alignment functionality by aligning the chunks of a read in parallel on a set of nodes and aggregating partial alignment results (AR) to an alignment result to be stored in the IMDB, and
   dynamically select an alignment algorithm from a set of alignment algorithms.

2. The computer-based system according to claim 1, further comprising:
   an updater framework configured to automatically download and import annotation updates from external sources into the IMDB.

3. The computer-based system according to claim 1, further comprising:
   a user interface (UI) including at least one genome browser, the genome browser comprising:
      a section configured to display a comparison of the nucleotide sequence and multiple referenced cell lines/genomes and/or a reference sequence,
      a section configured to display combined analysis information from multiple external databases, and
      a section configured to select instructions for data processing for specific pipeline configurations.

4. The system according to claim 3, wherein the specific pipeline configurations are an alignment of genomic sequence data.

5. A computer-implemented method for processing human or non-human nucleotide sequence data with an in-memory database (IMDB), the method comprising:
   providing a cluster with a set of computing nodes with multiple CPU cores, each implementing a worker for parallel data processing;
   providing the nucleotide sequence data as reads in the IMDB, the IMDB having a two-array index data structure including an array of entry points and an array of matching positions in a reference genome and being configured to integrate a plurality of alignment algorithms; and
   performing data processing concurrently to sequencing, wherein the data processing comprises:
      aligning chunks of a read in parallel on the set of computing nodes,
      assigning workers to the chunks depending on available processing power,
      dynamically selecting an alignment algorithm from the plurality of alignment algorithms to be executed by the worker, and aggregating partial alignment results (AR) to an alignment result to be stored in the IMDB.

6. The method according to claim 5, further comprising:
executing variant calling in parallel on the set of computing nodes and aggregating partial variant calling results (VCR) to a variant calling result, and
automatically analyzing the variant calling result by accessing an updater framework in the IMDB, wherein the updater framework regularly and automatically checks a plurality of different external annotation sources for updates and which automatically downloads and imports the updates in the IMDB.

7. The method according to claim 5, wherein the alignment is directly implemented in the IMDB.

8. The method according to claim 5, wherein the alignment is seed-based and a search strategy is used to evaluate matches for applying heuristics.

9. The method according to claim 5, wherein the alignment is based on heuristics to apply efficient algorithms to a first fraction of the reads and, optionally, to apply complex alignment algorithms to a second fraction of the reads.

10. The method according to claim 5, wherein hit lists are used for scoring previously found matches and/or hits.

11. The method according to claim 5, wherein first hit lists are handled separately from second hit lists, and wherein the first hit lists and the second hit lists are used for scoring of previously found matches and for finding new positions.

12. The method according to claim 5, wherein the alignment is based on a double indexing, in that hits from each of two subsequent seeds in the reference genome are combined and stored in a separate index structure once a configurable threshold for seed matches in two subsequent seeds is exceeded.

13. The method according to claim 5, wherein the alignment is executed on the workers in parallel on different processing nodes in a distributed system and beyond boundaries of a computer node or processor.

14. The method according to claim 5, wherein for the alignment each read is divided into non-overlapping seeds.

15. The method according to claim 5, wherein an index data structure is replicated over local memory of processor sockets or over multiple nodes of the cluster in order to allow for on-the-fly read alignments on a massive parallel machine.

16. A computer-based system for processing nucleotide sequence data, the computer-based system comprising:
a cluster of computing nodes configured to process data in parallel, each of the computing nodes including a plurality of central processing unit (CPU) cores and implementing a worker;
an in-memory database (IMDB) configured to store the nucleotide sequence data in an index data structure and to integrate a plurality of alignment algorithms; and
an alignment coordinator configured to provide the IMDB with a modified alignment functionality to permit the nucleotide sequence data to be stored in the IMBD in the index data structure, to permit an alignment of chunks of a read of the nucleotide sequence data in parallel on a selected set of computing nodes, to aggregate partial alignment results (AR) to an alignment result to be stored in the IMDB, to assign chunks to workers depending on available processing power of the workers, and to dynamically select an alignment algorithm from the plurality of alignment algorithms to be executed by the worker.

17. The method according to claim 16, wherein the index data structure is at least one of a single index data structure or a two-array index data structure stored in the IMDB.

18. The computer-based system according to claim 16, further comprising:
an updater framework configured to automatically download and import annotation updates from external sources into the IMDB.

19. The computer-based system according to claim 16, further comprising:
a user interface (UI) including at least one genome browser, the genome browser comprising:
a section configured to display a comparison of the nucleotide sequence and multiple referenced cell lines/genomes and/or a reference sequence;
a section configured to display combined analysis information from multiple external databases; and
a section configured to select instructions for data processing for specific pipeline configurations.

20. The computer-based system according to claim 19, wherein the specific pipeline configurations are an alignment of genomic sequence data.

* * * * *

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic DNA

<400> SEQUENCE: 1
actggattat atatgccgat cctgca                                26

<210> SEQ ID NO 2
<211> LENGTH: 25
<212> TYPE: DNA
<213> ORGANISM: Artificial Sequence
<220> FEATURE:
<223> OTHER INFORMATION: Synthetic DNA

<400> SEQUENCE: 2
ctcgattata tatgcggatt cctgc                                 25
```